United States Patent
Carlsson (10) Patent No.: US 10,391,336 B2
(45) Date of Patent: Aug. 27, 2019

(54) IMAGE GUIDED RADIOTHERAPY WITH ADJUSTED ANGULAR RANGE OF SOURCE

(71) Applicant: Elekta AB (publ), Stockholm (SE)

(72) Inventor: Per Carlsson, Täby (SE)

(73) Assignee: ELEKTA AB (PUBL), Stockholm (SE)

( * ) Notice: Subject to any disclaimer, the term of this patent is extended or adjusted under 35 U.S.C. 154(b) by 152 days.

(21) Appl. No.: 15/117,695

(22) PCT Filed: Feb. 4, 2015

(86) PCT No.: PCT/EP2015/052322
§ 371 (c)(1),
(2) Date: Aug. 9, 2016

(87) PCT Pub. No.: WO2015/118021
PCT Pub. Date: Aug. 13, 2015

(65) Prior Publication Data
US 2016/0354617 A1 Dec. 8, 2016

(30) Foreign Application Priority Data
Feb. 10, 2014 (GB) .................................. 1402270.1

(51) Int. Cl.
*A61N 5/10* (2006.01)
(52) U.S. Cl.
CPC ............ *A61N 5/1082* (2013.01); *A61N 5/103* (2013.01); *A61N 5/1049* (2013.01); *A61N 5/1067* (2013.01); *A61N 2005/1061* (2013.01)
(58) Field of Classification Search
CPC ........... A61B 6/00; A61B 6/44; A61B 6/4429; A61B 6/435; A61B 6/4441; A61B 6/4447;
(Continued)

(56) References Cited

U.S. PATENT DOCUMENTS 7,847,275 B2 * 12/2010 Lifshitz ................. A61B 6/032
250/491.1
2005/0234327 A1 * 10/2005 Saracen ............... A61B 6/0457
600/407
(Continued)

FOREIGN PATENT DOCUMENTS

EP 1 832 312 A1 9/2007
EP 2 623 155 A1 8/2013
(Continued)

OTHER PUBLICATIONS

International Search Report and Written Opinion in International Application PCT/EP2015/052322, dated Mar. 27, 2015.
(Continued)

*Primary Examiner* — Anastasia Midkiff
(74) *Attorney, Agent, or Firm* — Finnegan, Henderson, Farabow, Garrett & Dunner LLP (57) ABSTRACT

An apparatus comprises a radiotherapy delivery apparatus having a radiation source for emitting a beam of radiation and wherein the source is rotatable around an axis intersecting the beam through a range of at least x degrees, an imaging device, and a control unit controlling the source and imaging device. The apparatus further comprises a treatment planning computer receiving a first image of a patient, and parameters defining the operations of the radiotherapy delivery apparatus. Parameters include an available range of rotation for the source, x-e, where e>0. The treatment planning computer generates a treatment plan for the patient based on the received image and parameters. The control unit determines a patient position using the imaging device, determines a rotation r of the patient around the axis relative to the first image, and compensates for the rotation by offsetting the source by a rotation, r, when r<e.

20 Claims, 6 Drawing Sheets

(58) Field of Classification Search
CPC ....... A61B 6/4452; A61B 6/4476; A61B 6/50; A61B 6/501; A61B 6/54; A61B 6/58; A61B 6/582; A61B 6/587; A61B 6/589; A61B 34/00; A61B 34/20; A61B 34/70; A61B 2034/2046; A61B 2560/00; A61B 2560/02; A61B 2560/0266; A61B 2560/04; A61B 2560/0443; A61N 5/10; A61N 5/103; A61N 5/1042; A61N 5/1048; A61N 5/1049; A61N 5/1064; A61N 5/1065; A61N 5/1067; A61N 5/1075; A61N 5/1077; A61N 5/1081; A61N 5/1082; A61N 2005/1601; A61N 2005/1092; G01T 1/29; G01T 1/2907; G01T 1/2914; G01T 1/2921; G01T 7/00; G01T 7/005; G01N 23/00; G01N 23/02; G01N 23/04; G01N 23/046; G01N 23/06; G01N 23/083; G01N 2223/00; G01N 2223/03; G01N 2223/04; G01N 2223/20; G01N 2223/30; G01N 2223/302–2223/308; G01N 2223/32; G01N 2223/321; G01N 2223/33; G01N 2223/3303; G01N 2223/40; G01N 2223/401; G01N 2223/419; G01N 2223/421; G01N 2223/425; G06T 7/00; G06T 7/0002; G06T 7/0012; G06T 7/0014; G06T 7/10; G06T 7/13; G06T 7/136; G06T 7/174; G06T 7/20; G06T 7/245; G06T 7/254; G06T 7/30; G06T 7/38; G06T 7/60; G06T 7/62; G06T 7/70; G06T 7/73; G06T 7/97; G06T 2207/00; G06T 2207/10; G06T 2207/10072; G06T 2207/10081; G06T 2207/20; G06T 2207/20212; G06T 2207/21224; G06T 2207/30; G06T 2207/3004; G06T 2207/30016; G06T 2211/00; G06T 2211/40; G06T 2211/436; G06T 2210/41; H01J 37/00; H01J 37/02; H01J 37/023; H01J 37/20; H01J 37/30; H01J 37/3002; H01J 37/3005; H01J 37/302; H01J 37/3023; H01J 37/3026; H01J 37/304; H01J 37/3045; H01J 2235/00; H01J 2235/16; H01J 2235/161; H01J 2235/162; H01J 2237/00; H01J 2237/02; H01J 2237/0203; H01J 2237/024; H01J 2237/0245; H01J 2237/04; H01J 2237/15; H01J 2237/1501–2237/1506; H01J 2237/20; H01J 2237/22; H01J 2237/221; H01J 2237/245; H01J 2237/2457; H01J 2237/24578; H01J 2237/24592; H01J 2237/248; H01J 2237/2485; H01J 2237/2487; H01J 2237/30; H01J 2237/304; H01J 2237/30405; H01J 2237/30411; H01J 2237/30433; H01J 2237/30438; H01J 2237/30455; H01J 2237/30466; H01J 2237/30472

See application file for complete search history.

(56) References Cited

U.S. PATENT DOCUMENTS

| | | |
|---|---|---|
| 2006/0072699 A1 | 4/2006 | Mackie et al. |
| 2009/0003975 A1* | 1/2009 | Kuduvalli ............ A61N 5/1049 414/146 |
| 2011/0210261 A1* | 9/2011 | Maurer, Jr. .............. A61N 5/10 250/393 |
| 2012/0035462 A1* | 2/2012 | Maurer, Jr. .......... A61B 6/5247 600/411 |
| 2013/0131430 A1 | 5/2013 | Froehlich et al. |
| 2013/0142310 A1 | 6/2013 | Fahimian et al. |
| 2014/0094643 A1* | 4/2014 | Gall ...................... H05H 13/02 600/2 |

FOREIGN PATENT DOCUMENTS

| | | |
|---|---|---|
| JP | 2002 248176 A | 9/2002 |
| WO | WO 2005/041774 A1 | 5/2005 |

OTHER PUBLICATIONS

United Kingdom Search Report in Application GB 1402270.1, dated Aug. 20, 2014.

* cited by examiner

IMAGE GUIDED RADIOTHERAPY WITH ADJUSTED ANGULAR RANGE OF SOURCE

CROSS-REFERENCE TO RELATED APPLICATION

This application is a national phase of International Application No. PCT/EP2015/052322, filed on Feb. 4, 2015, which claims priority to GB Application No. 1402270.1, filed on Feb. 10, 2014. The contents of the above-reference applications are expressly incorporated herein by reference in their entireties.

FIELD OF THE INVENTION

The present invention relates to image guided radiotherapy.

BACKGROUND ART

Radiotherapy is a process for the treatment of lesions such as cancers, which involves directing a beam of ionising radiation (typically high-energy x-rays) towards the lesion. Care is taken to maximise the dose that is applied to the lesion and minimise the dose that is applied to the areas of healthy tissue around the lesion, mainly by directing the beam toward the lesion from a multitude of directions and collimating the beam (i.e. shaping its cross-section) as required depending on the shape of the lesion. Various protocols exist for determining the beam directions, shapes, strengths and times to deliver a specific three-dimensional dose distribution to a specific region of the patient.

Clearly, it is necessary to ensure that the dose distribution is positioned correctly within the patient, i.e. that the patient and the radiotherapy apparatus are correctly. aligned. To do this, it is now common to take a cone-beam CT scan ("CBCT") before treatment starts, and use that scan to compare the actual patient position with the treatment coordinate system to detect any mismatch. That is measured and calculated in 6 degrees of freedom, and the patient position is adjusted so as to match that which is expected by treatment coordinate system. For this purpose, patient table are known which are adjustable in 6 degrees of freedom, i.e. three translational directions and three rotational directions. This allows the patient to be brought into position with the apparatus, placing the location expected by the apparatus and at which the dose distribution will be delivered.

SUMMARY OF THE INVENTION

A table with 6 degrees of freedom imposes a significant cost on the apparatus, and inevitably has a redundant axis. The provision for multiple degrees of freedom also adds to the volume of the table and its supporting structure, which can give clearance problems during treatment.

It is also inherently undesirable to rotate the patient on the table, at least around horizontal axes, Significant rotations are disconcerting for the patient, and any rotation will result in gravity acting differently on the patient, which could give rise to positional deviations in the patient anatomy relative to the bed.

The present invention therefore provides a way of dealing with rotation of the patient in an axis about which the source has a limited range of rotation, without needing a rotational adjustment of the table. The invention thus provides an apparatus comprising a radiotherapy delivery apparatus having a radiation source adapted to emit a beam of radiation and to rotate around at least one axis that intersects with the beam, the rotation being confined to a limited range of rotation, an associated imaging device, and a control means controlling both the source and the imaging device, together with a treatment planning computer that accepts an image of a patient and parameters defining the machine capabilities, and creates a treatment plan based on both, wherein the source is capable of rotation in that axis through a range of at least x degrees, and a parameter is passed to the treatment planning computer defining the source's available range as x-e where e>0, and the control means is adapted to detect the patient position using the imaging device, determine a rotation r of the patient around the axis relative to the image used by the treatment planning computer, and if r<e compensate for the rotation by offsetting the source by a rotation equal to r.

Clearly, if r>e then the system should stop with an appropriate error report as the mispositioning of the patient is too great to correct for automatically.

The image of a patient can be a CT scan, an MRI scan, or the like. It can be obtained via the imaging device, or by a separate diagnostic or imaging device.

The imaging device can be integrated with the source, for example by both being mounted on a rotatable gantry—ideally a common gantry carrying both.

The control means can determine the rotation r by obtaining a further image of the patient using the imaging device. The further image can be a CT scan, or an MRI scan, or an ultrasound scan, or can be a visual image of the patient. The control means can then determine the rotation r by comparing the image and the further image such as by a co-registration process.

The limited range of rotation is typically less than 360 degrees although this need not necessarily be the case. An example of the type of radiotherapy apparatus to which this invention is applicable is shown in our earlier patent application WO2005/041774, but it can equally be applied to other types.

BRIEF DESCRIPTION OF THE DRAWINGS

An embodiment of the present invention now be described by way of example, with reference to the accompanying figures in which.

DETAILED DESCRIPTION OF THE EMBODIMENTS

Figure 1:
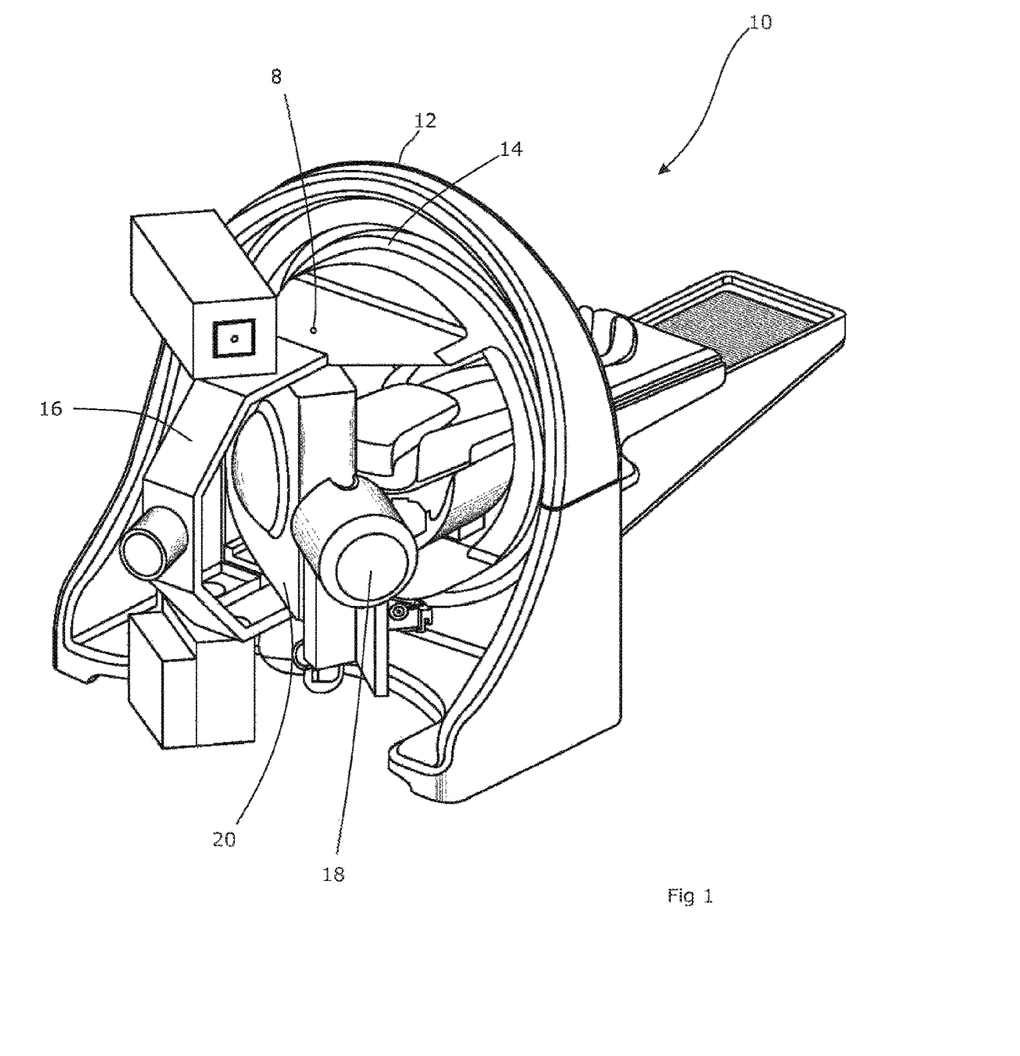
FIG. 1 shows a radiotherapy apparatus according to WO2005/041774, being one example of the type of apparatus to which the present invention can be applied.

FIG. 1 illustrates the radiotherapy apparatus described in WO2005/041774, to which the reader is referred for a fuller description. In brief, the apparatus 10 comprises a substantially vertical circular outer ring structure 12 which is rigidly fixed to a floor structure in order to provide a firm base. An inner ring 14 is journalled within the outer ring 12 so that it can rotate about a horizontal axis, transverse to the outer ring 12 and passing through the centre of the circular ring. A U-profile support 16 is attached at either end to the inner ring 14 and extends out of the plane of the inner ring 14.

A linear accelerator 18 is supported on a mounting 20 that is carried by the U-profile support 16. The mounting 20 is attached to the support 16 via a pair of pivot connections 8, defined on opposing arms of the U-profile support 16 that extend out of the plane of the inner ring 14. These allow the mounting 20 to rotate relative to the support 16 about an axis that is perpendicular to the horizontal axis of the inner ring 14, and offset from the inner ring 14. The orientation of the axis in the vertical plane will of course depend on the instantaneous rotational position of the inner ring 14. The two axes—i.e. the perpendicular axis of the mounting and the horizontal axis of the inner ring meet at a defined point, which remains fixed due to the geometry described above. The linear accelerator 18 is attached to the mounting 20 and directs a beam of radiation towards the defined point. Thus, it will be appreciated that whatever the rotational positions of the inner ring 14 and the mounting 20, the beam will be directed towards the defined point. However, the direction from which the beam arrives at the defined point will be dictated by those rotational positions.

Electrical motors are provided in order to drive the inner ring 14 relative to the outer ring 12, and the mounting 20 relative to the support 16. These are servo-controlled so that specific chosen positions can be instructed and maintained.

Figure 2:
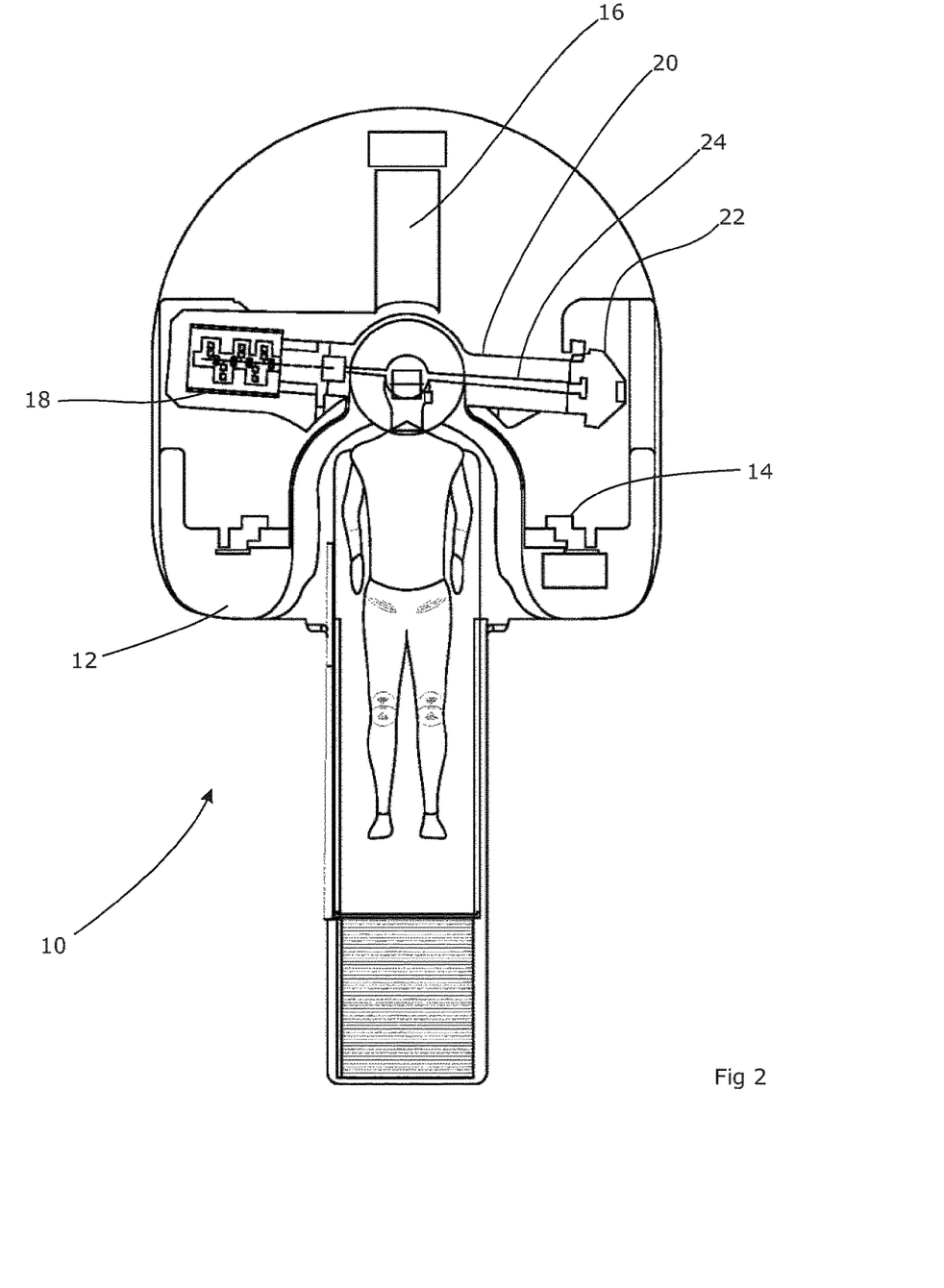
FIG. 2 shows the apparatus of FIG. 1, in a horizontal section.
Figure 3:
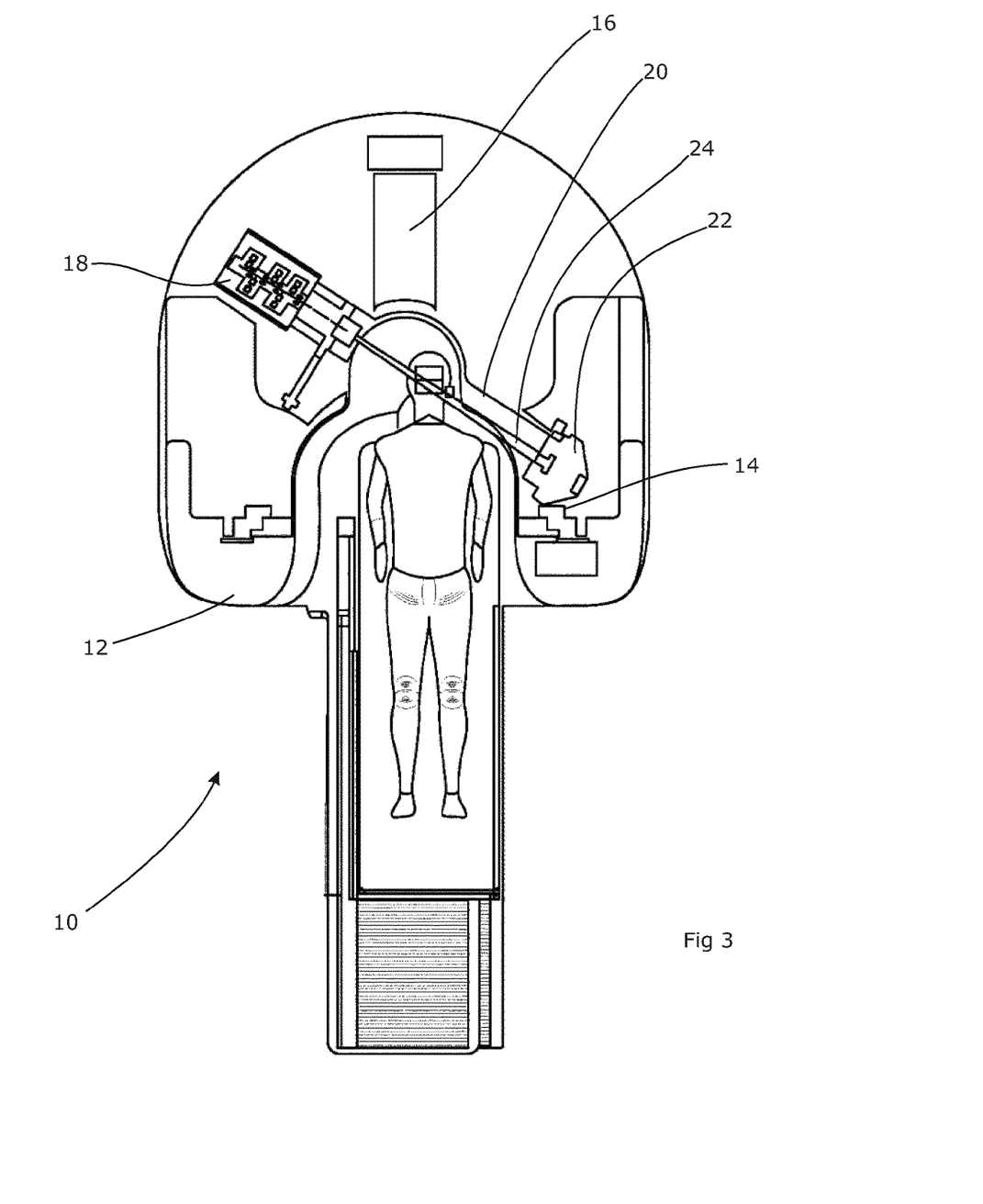
FIG. 3 shows the apparatus of FIG. 1 in a horizontal section, after rotation of the radiation source in a horizontal plane.

FIGS. 2 and 3 show the apparatus from above, with the inner ring 14 oriented so that the perpendicular axis is vertical and thus aligned with the view direction. FIG. 2 shows the mounting 20 at its extreme anti-clockwise position and FIG. 3 at its extreme clockwise position. FIGS. 2 and 3 also show the beam stop 22 provided on the mounting 20 opposite the linear accelerator 18 in order to absorb the beam 24 that is produced and prevent it from escaping the apparatus.

As can be seen, in order to avoid collisions between elements of the structure, especially as between the linear accelerator 18 and the inner ring 14, or the beam stop 22 and the inner ring 14, the total rotational extent in this axis is limited to about 45 degrees.

Figure 4:
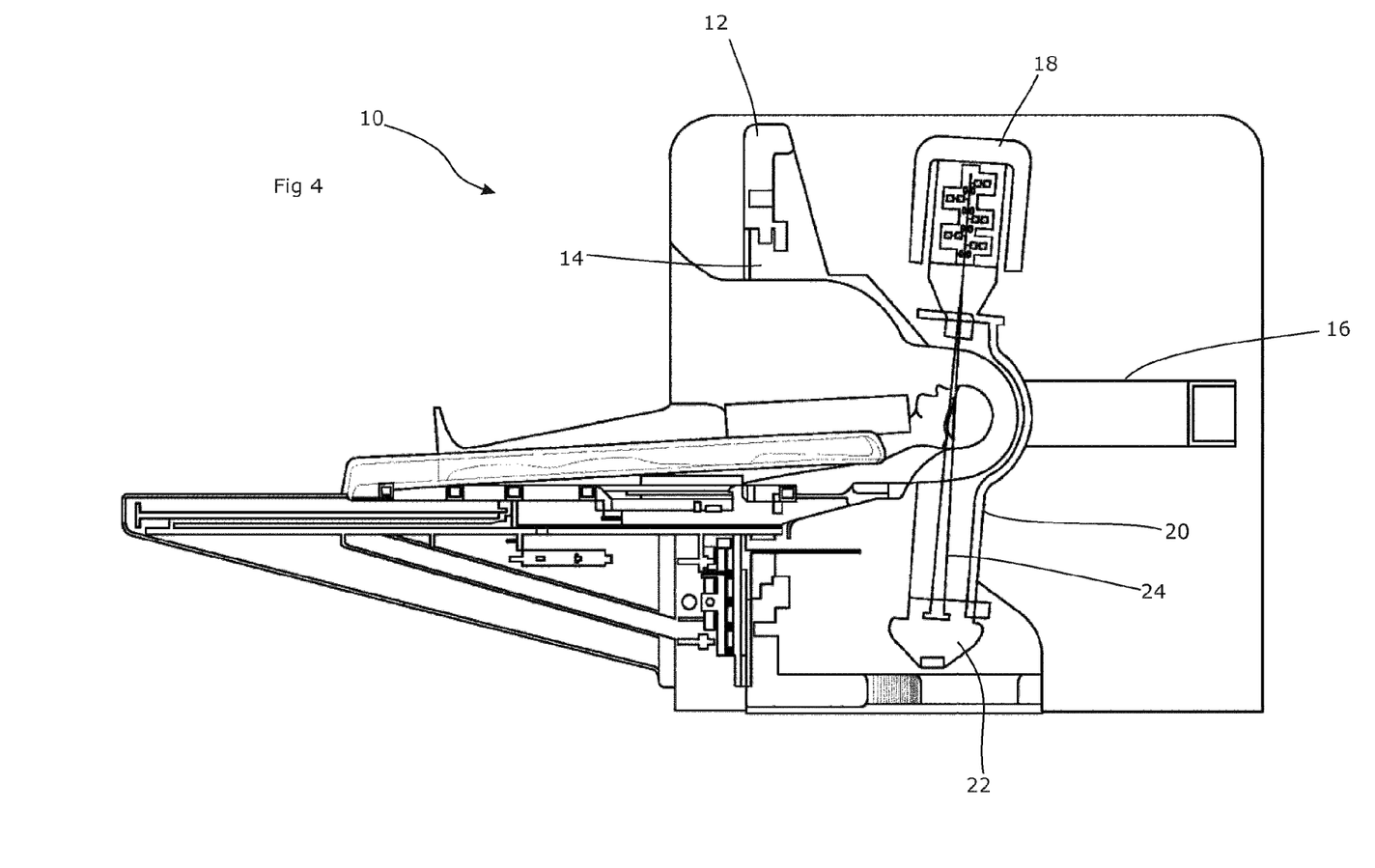
FIG. 4 shows the apparatus of FIG. 1, in a vertical section.
Figure 5:
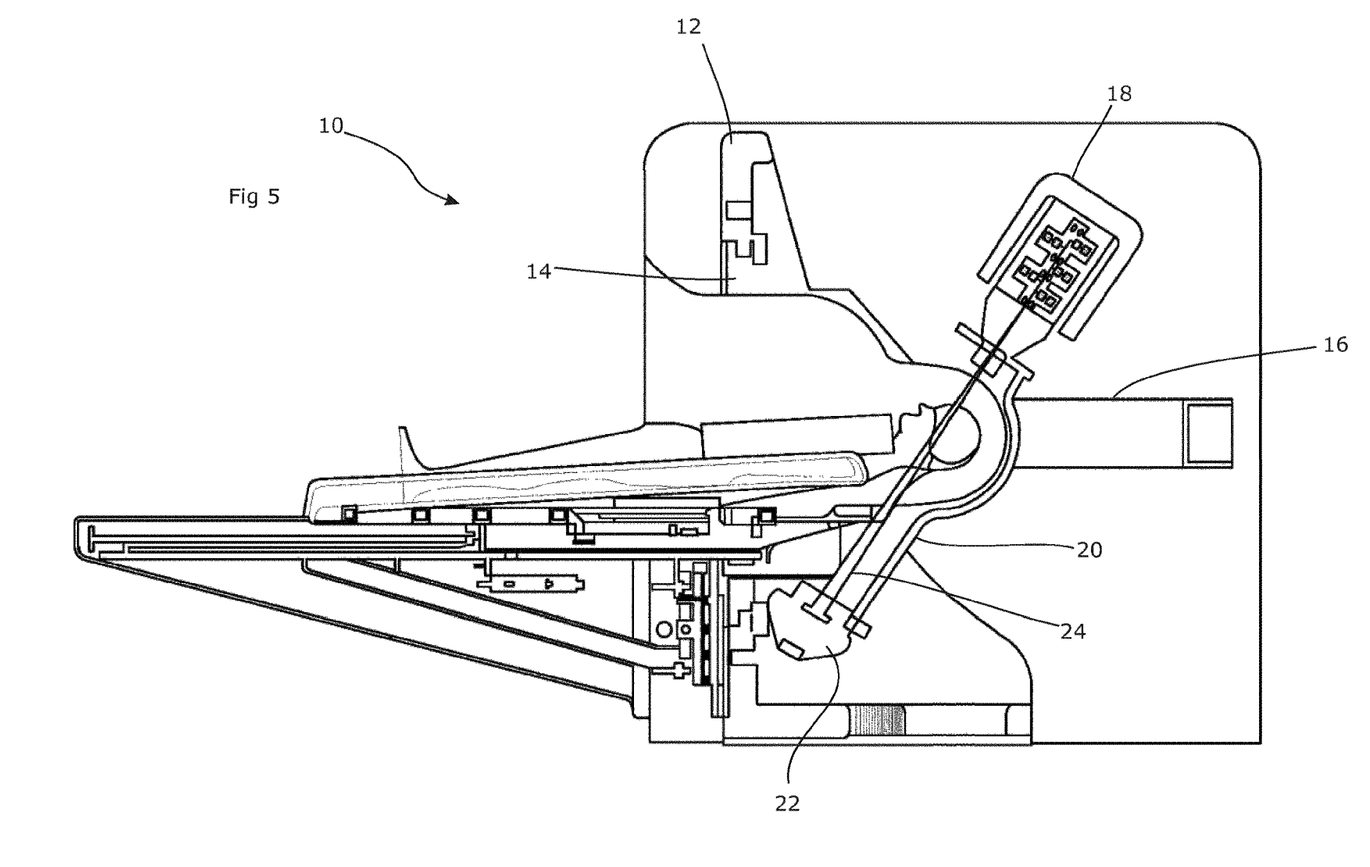
FIG. 5 shows the apparatus of FIG. 1 in a vertical section, after rotation of the radiation source in a vertical plane.

FIG. 4 shows the apparatus from one side. Relative to the state shown in FIGS. 2 and 3, the inner ring 14 has been rotated through 90° in order to place the perpendicular axis horizontal, i.e. into and out of the page. FIG. 4 shows the apparatus with the linear accelerator 18 at its highest point, emitting a near-vertical beam 24 through the patient's head and into the beam stop 22. FIG. 5 shows the apparatus with the mounting 20 rotated through a maximum angle of about 45°. Once again, it can be seen that there are necessary limits on the maximum rotation of the structure, so as to prevent collisions with other parts of the apparatus.

Careful design of the apparatus can be useful in extending these limits of rotation, and the use of alternative structures for the radiotherapy apparatus may create a very different pattern of rotational limitations. For example, a rotatable C-arm structure may have rotational limits of close to or exceeding 360° when rotating around the longitudinal (cranio-cordal) axis of the patient (often referred to as the Z-axis) and limits of ±45° around an axis transverse to the longitudinal axis. It should be emphasised, therefore, that the invention is not limited to the above-described structure, which may be varied in many ways or replaced entirely with a different structure subject to limits on rotation around the patient.

This limitation as to rotation is taken into consideration at the treatment planning stage, along with other limitations such as maximum output dose rate, maximum rotation speed in each axis, maximum rate of collimator movement, maximum aperture, etc, Treatment planning is a process starting with a three-dimensional image of the patient (for example a CT scan) which has been segmented by a physician to identify volumes corresponding to the lesion, sensitive tissues that must be protected from overdose, and other tissues. An iterative mathematical process is then applied by a treatment planning computer, resulting in a sequence of beams that the apparatus is capabie of emitting without breaching its various limitations and which will, collectively, deliver the desired dose distribution to the patient volume.

In theory, the patient is then placed on the patient support and the dose is applied by the radiotherapy apparatus. However, in practice there is often a delay between the CT scan being taken and the treatment commencing. Also, the CT scanning apparatus with which the scan was prepared may not be the same apparatus as is used for delivery of the radiotherapy. Thus, the patient will have left the apparatus on which the scan was taken and will have been re-positioned ready for treatment. Some difference in positioning as between the two episodes is likely or inevitable. As noted above, this is usually corrected by way of a moveable patient support that is able to adjust the position of the patient in six degrees of freedom in order to correct for positional errors. To determine the correction that is needed, a brief CT or x-ray image is taken of the patient immediately prior to treatment, or a visual determination is made of the patient position using (for example) illuminated markers on the patient's anatomy, or another means is used to determine the patient position. This is then compared to the position of the patient in the original CT scan used for treatment planning, and a displacement is obtained. The correction is then simply the reverse of that displacement so as to return the patient to the position for which the treatment was planned.

According to the invention, rotational errors around an axis that corresponds to a rotational axis of the radiotherapy apparatus are instead corrected by offsetting the radiotherapy apparatus during treatment. To accommodate this within the limited rotation of the apparatus, the treatment planning computer is told that the available range of rotation in that axis is less than the actual available range, by a small factor or overstroke of about 5 degrees. This means that during treatment, this overstroke is available to the apparatus for positional correction. In practice, this means that having measured the angular deviation of the target versus the linac coordinate system, this deviation is to be used as an input to the linac head control system. The motion of the linac compared to the original axis will then be according to the treatment plan but with the addition (or subtraction) of a constant offset movement.

Figure 6A:
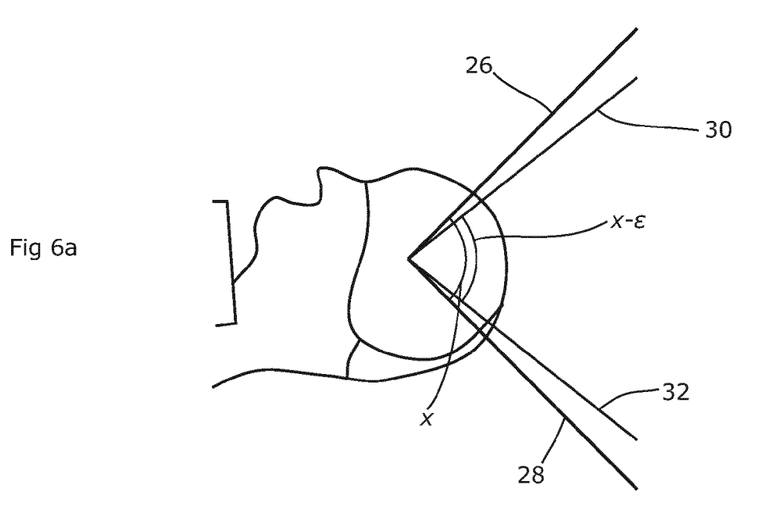
FIGS. 6a and 6b illustrate the operating principle of the invention.
Figure 6B:
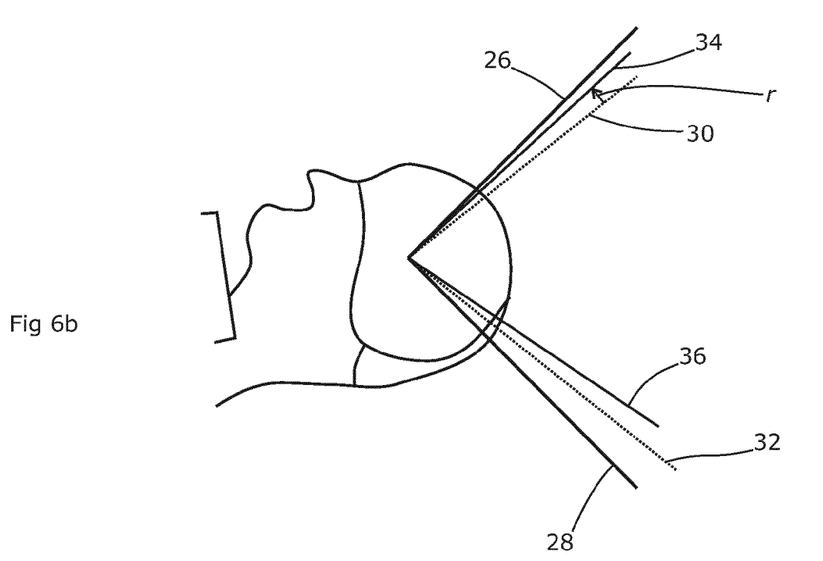

This is illustrated in FIGS. 6a and 6b, which show a side view of a patient's head during radiotherapy. The angular range of beam directions of which the apparatus is capable in this plane is shown by the upper limit 26 and the lower limit 28, defining an angle x between them. For the purposes of treatment planning, however, the treatment planning computer is programmed to work with a narrower angular range, lying between a reduced upper limit 30 and a reduced lower limit 32 which define a lesser angle x-ε between them. Thus, relative to the angular range used for treatment planning purposes, the apparatus is in fact capable of an overstroke of ε.

When treatment is ready to start and the patient has been positioned within (or on) the apparatus, the patient's actual position is determined and the translational and angular errors relative to the position during imaging is determined. The translational errors can be corrected easily with linear movement of the patient support in a known manner. Rotational errors can be corrected for using the overstroke, without requiring a rotational adjustment of the patient support. If the error in the plane of FIG. 6b is r, then this angle can be added to each of the rotational positions from which radiotherapy is delivered. In effect, the working range of the apparatus is moved from the reduced upper limit 30 and the reduced lower limit 32 to a revised upper limit 34 and a revised lower limit 36, which are separated from the reduced limits 30, 32 by an angle r. Provided that r<ε, the resulting working range will still be within the actual upper and lower limits 26, 28 of the apparatus.

A corresponding adjustment can be made in other planes of rotation. Errors consisting of rotations around a vertical axis can alternatively (or in addition) be corrected by rotation of the patient support, as rotation in this axis is much more straightforward to engineer as the support remains level. Equally, where the rotation of the apparatus is constrained in one or more axis but free in one or more other axes, then this technique can be applied in the former axes and other techniques applied in the remaining axes.

This overstroke is much cheaper to achieve than a patient support with the necessary six degrees of freedom, such as one incorporating a hexapod. Translational movements of the patient are relatively easy to engineer, and if the radiotherapy apparatus allows rotation of the source in two axes (as shown in FIGS. 1 to 5) then this leaves only one further rotational axis that may need correction. Typically, this will be rotation of the patient around a vertical axis, which is also easy to engineer.

It will of course be understood that many variations may be made to the above-described embodiment without departing from the scope of the present invention.

The invention claimed is:

1. An apparatus comprising:
    a radiotherapy delivery apparatus comprising:
        a radiation source configured to emit a beam of radiation, the radiation source being rotatable around an axis intersecting the beam and having a first range of rotation;
        an imaging device configured to detect a patient position; and
        a control unit for controlling the radiation source and the imaging device; and
    a treatment planning computer configured to:
        receive a first image of a patient;
        receive parameters defining the operations of the radiotherapy delivery apparatus, wherein the parameters include a predefined available range of rotation for the radiation source, wherein the predefined available range is equal to the first range less a first nonzero angle; and
        generate a treatment plan for the patient based on the first image and the received parameters;
    wherein the control unit is configured to:
        receive a second image of the patient from the imaging device;
        determine, by comparing the first image and the second image, a rotation of the patient relative to the axis; and
        compensate for the patient rotation by rotating the radiation source by a rotation equal to the rotation of the patient when an amount of the rotation is less than the first nonzero angle.

2. The apparatus according to claim 1, wherein the first image is a CT scan.

3. The apparatus according to claim 1, wherein the first image is received from the imaging device.

4. The apparatus according to claim 1, wherein the radiation source and the imaging device are both mounted on a rotatable gantry.

5. The apparatus according to claim 4, wherein the radiation source and the imaging device are mounted on the same rotatable gantry.

6. The apparatus according to claim 1, wherein the second image is a CT scan.

7. The apparatus according to claim 1, wherein the range of rotation of the radiation source is less than 360 degrees.

8. The apparatus according to claim 1, wherein the control unit is configured to generate an alert when an amount of the patient rotation is greater than the first nonzero angle.

9. The apparatus according to claim 1, wherein comparing the first image and the second image comprises performing an image co-registration process.

10. A system for radiotherapy treatment, comprising:
    a radiotherapy delivery apparatus comprising:
        a radiation source configured to emit a beam of radiation, the radiation source being rotatable around an axis intersecting the beam and having a first range of rotation; and
        a control unit for controlling the radiation source; and
    a treatment planning computer configured to:
        receive a first image of a patient;
        receive parameters defining the operations of the radiotherapy delivery apparatus, wherein the parameters include a predefined available range of rotation for the radiation source, wherein the predefined available range is equal to the first range less a first nonzero angle; and
        generate a treatment plan for the patient based on the first image and the received parameters;
    wherein the control unit is configured to:
        receive a second image of the patient from an imaging device;
        determine, by comparing the first image and the second image of the patient, a rotation of the patient relative to the axis; and
        compensate for the patient rotation by rotating the radiation source by a rotation equal to the rotation of the patient when an amount of the rotation is less than the first nonzero angle.

11. The system according to claim 10, wherein the first image is a CT scan.

12. The system according to claim 10, wherein the first image is received from the imaging device.

13. The system according to claim 10, wherein the radiation source and the imaging device are both mounted on a rotatable gantry.

14. The system according to claim 10, wherein the second image of the patient is a CT scan.

15. The system according to claim 10, wherein the range of rotation of the radiation source is less than 360 degrees.

16. The system according to claim 10, wherein the control unit is configured to generate an alert when an amount of the patient rotation is greater than the first nonzero angle.

17. The system according to claim 10, wherein comparing the first image and the second image comprises performing an image co-registration process.

18. A computer-implemented method comprising the following operations:
- receiving a first image of a patient from an imaging device;
- receiving parameters defining the operations of a radiotherapy delivery apparatus configured to emit a beam of radiation from a radiation source, wherein the parameters include a predefined available range of rotation for the radiation source equal to a first range less a first nonzero angle, wherein the first range is an angular range of rotation that the radiation source is rotatable around an axis intersecting the beam;
- generating a treatment plan for the patient based on the first image and the received parameters;
- receiving a second image of the patient from the imaging device;
- determining, by comparing the first image and the second image, a rotation of the patient relative to the axis; and
- compensating for the patient rotation by rotating the radiation source by a rotation equal to the rotation of the patient when an amount of the rotation is less than the first nonzero angle.

19. The computer-implemented method according to claim 18, further comprising generating an alert when an amount of the patient rotation is greater than the first nonzero angle.

20. The computer-implemented method according to claim 18, wherein comparing the first image and the second image comprises performing an image co-registration process.

* * * * *